(12) United States Patent
Nguyen et al.

(10) Patent No.: US 11,192,086 B2
(45) Date of Patent: Dec. 7, 2021

(54) REUSE AND RECYCLING FOR POLYMER SYNTHESIS

(71) Applicant: MICROSOFT TECHNOLOGY LICENSING, LLC, Redmond, WA (US)

(72) Inventors: Bichlien Hoang Nguyen, Seattle, WA (US); Karin Strauss, Seattle, WA (US); Douglas P. Kelley, Sammamish, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 198 days.

(21) Appl. No.: 16/443,637

(22) Filed: Jun. 17, 2019

(65) Prior Publication Data

US 2020/0391175 A1    Dec. 17, 2020

(51) Int. Cl.
*B01J 19/00*      (2006.01)
*B01J 19/06*      (2006.01)
(Continued)

(52) U.S. Cl.
CPC ....... *B01J 19/2465* (2013.01); *B01J 19/0006* (2013.01); *B01J 19/06* (2013.01);
(Continued)

(58) Field of Classification Search
CPC .... B01J 19/00; B01J 19/0006; B01J 19/0046; B01J 19/06; B01J 19/24; B01J 19/245; B01J 19/2455; B01J 19/2465; B01J 2219/00; B01J 2219/00049; B01J 2219/00186; B01J 2219/00274; B01J 2219/00277; B01J 2219/000351; B01J 2219/00353; B01J 2219/00418; B01J 2219/00583; B01J 2219/00585; B01J 2219/0059; B01J 2219/0068;
(Continued)

(56) References Cited

U.S. PATENT DOCUMENTS 9,322,063 B2 * 4/2016 Zhao ............... C12Q 1/6874
2003/0003222 A1   1/2003 Bass et al.
(Continued)

OTHER PUBLICATIONS

"International Search Report and Written Opinion Issued in PCT Application No. PCT/US20/030004", dated Jul. 21, 2020, 10 Pages.

*Primary Examiner* — Natasha E Young
(74) *Attorney, Agent, or Firm* — Newport IP, LLC; Benjamin A. Keim (57) ABSTRACT

Reagents and solvents used for polymer synthesis are reused or recycled rather than discarded. The outflow from each step of polymer synthesis may be collected separately in one of multiple dedicated containers. Reuse returns the outflow from a step of polymer synthesis back to an input of a polymer synthesizer for subsequent use in that same step. Recycling processes the outflow from one or more steps of polymer synthesis to restore original concentrations or purity levels for use in a later synthesis run. Quality control analysis may determine if outflow collected from a polymer synthesizer is reused or recycled. These techniques reduce reagent cost and waste quantity. These techniques may be used with phosphoramidite or enzyme-based synthesis of deoxyribonucleic acid (DNA).

19 Claims, 6 Drawing Sheets

(51) Int. Cl.
    *B01J 19/24*    (2006.01)
    *C07H 1/02*     (2006.01)
    *C12P 19/34*    (2006.01)

(52) U.S. Cl.
    CPC .............. *B01J 19/245* (2013.01); *C07H 1/02* (2013.01); *C12P 19/34* (2013.01); *B01J 2219/00186* (2013.01)

(58) Field of Classification Search
    CPC .... B01J 2219/00693; B01J 2219/00695; B01J 2219/00718; B01J 2219/0072; B01J 2219/00722; B01J 2219/00725; C07H 1/00; C07H 1/02; C12P 19/00; C12P 19/26; C12P 19/28; C12P 19/30; C12P 19/34
    See application file for complete search history.

(56) References Cited

U.S. PATENT DOCUMENTS

| | | |
|---|---|---|
| 2008/0262172 A1 | 10/2008 | Zhao |
| 2009/0093625 A1 | 4/2009 | Chi et al. |
| 2018/0016609 A1* | 1/2018 | Chen ..................... C07H 19/12 |

* cited by examiner

REUSE AND RECYCLING FOR POLYMER SYNTHESIS

BACKGROUND

The reagents and solvents used for polymer synthesis can be expensive and hazardous. Flow-through synthesis techniques use an excess of reagents to drive polymer synthesis forward. The leftover reagents and solvents that flow out a synthesis chamber are collected together after each synthesis run as waste. The combined waste stream from phosphoramidite synthesis of deoxyribose nucleic acid (DNA), for example, contains nucleoside phosphoramidites (i.e., A, G, C, and T phosphoramidites) and acetonitrile. The nucleoside phosphoramidite monomers are expensive reagents. Acetonitrile is toxic and highly flammable. Other techniques for DNA or for other polymers may also include reagents and solvents that are expensive and/or hazardous.

One relatively new use for DNA (as well as other types of polymers) is digital data storage. Digital data storage using DNA encodes the sequence of zeros and ones from digital data into a sequence of nucleotide monomers in a strand of DNA. Many thousands or millions of strands of DNA are typically used to encode a single computer file. Data centers that store petabytes of data in DNA strands may need to synthesize large quantities of DNA. This is in contrast to DNA synthesis for most biochemical and biological experiments which is often performed on the 40 nmol scale or lower. For small-scale DNA synthesis, the volume of waste is minimal and generally discarded without further consideration.

It is with respect to these and other considerations that the disclosure made herein is presented.

SUMMARY

This disclosure provides systems and techniques for reusing and recycling both reagents and solvents used in polymer synthesis. After each step of polymer synthesis, the reagents and solvents may be collected in dedicated containers rather than a combined waste tank. Each dedicated container may collect the outflow from a separate step of polymer synthesis that primarily contains a single reagent or wash solution. The contents of one of the dedicated containers may be reused in the same polymer synthesizer or recycled for use in the same or different polymer synthesizer.

Reuse refers to moving a solution collected from the outflow of polymer synthesis back to an input of the polymer synthesizer to be used again. Reuse occurs relatively quickly. A reagent or wash solution may be reused multiple times during the same synthesis run. Returning the same liquid collected from the outflow of a polymer synthesizer to an appropriate input of the polymer synthesizer without processing or modification is an example of reuse. Reuse may also include addition of concentrated reagents or solvents to the outflow collected in one of the dedicated containers to maintain an effective concentration within a predetermined concentration range.

Recycling refers to processing that may be more complex and take more time than reuse. Recycling may adjust the effective concentration, purify, filter, and/or clean outflow collected from a polymer synthesizer. Recycling is generally not performed as part of a synthesis run and may be done using an apparatus that is separate from the polymer synthesizer. Any processing that is not able to be completed within the time scale of a synthesis run may be characterized as recycling. There are no time restrictions for recycling. One example of recycling is distillation of a wash solution to recover solvent.

Collection of the outflow from separate steps of polymer synthesis in separate dedicated containers provides discrete "waste" streams for reuse or recycling. However, these outflows are not true waste streams because they are reused or recycled. Thus, the reagents and solvents that were previously used once and then discarded may be used multiple times. Unincorporated monomer subunits may be returned to a synthesis chamber and used to build a polymer strand rather than being discarded. This reduces reagent cost. Potentially hazardous organic solvents may be recycled and used in a later synthesis run reducing the volume of waste. This creates a less expensive and greener process for synthesizing polymers. The benefits of these improvements are particularly significant for large-scale polymer synthesis operations such as, for example, a DNA data storage center that continuously runs multiple oligonucleotide synthesizers to create a large number of DNA strands for storing digital data such as computer files.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. References made to individual items of a plurality of items can use a reference number with a letter of a sequence of letters to refer to each individual item. Generic references to the items may use the specific reference number without the sequence of letters.

DETAILED DESCRIPTION

This disclosure provides techniques, devices, apparatuses, and systems for reusing and recycling reagents and solvents used in polymer synthesis. The contents of this disclosure may be used with any type of polymer synthesis in which excess reagents, washes, solvents, etc. are flowed across a structure in which the polymers are synthesized. Depending on the specific synthesis technique, polymers may be synthesized on a flow cell, a column, an electrode array, or other structure.

Polymeric molecules ("polymers") as used herein include any type of polymers such as biological molecules and artificial polymers. Polymeric molecules that are based on or derived from biological molecules include DNA, ribonucleic acid (RNA), and proteins. The remainder of this disclosure primarily describes applications for the synthesis of DNA. However, the systems and methods for reuse and recycling of reagents and solvents are not necessarily limited to the synthesis of DNA and may be used for the synthesis of any type of polymer.

Techniques for DNA synthesis include the nucleoside phosphoramidite method and enzymatic DNA synthesis using the enzyme terminal deoxynucleotidyl transferase (TdT). Techniques for enzymatic RNA synthesis include using enzymes such as Phi6 RNA Replicase and TdT. Techniques for chemical protein synthesis involve coupling the carboxyl group or C-terminus of one amino acid to the amino group or N-terminus of another. One common technique for chemical protein synthesis is solid-phase synthesis of peptides. A brief description of each of these techniques for polymer synthesis is provided below.

Each of the synthesis techniques applies solutions of reagents (e.g., solutions of monomer subunits), washes, solvents, etc. in a specific sequence to a location where the polymers are being synthesized and much of the solution flows off without reacting with the growing polymer strands. Thus, a large percentage of the reagents are not consumed, and the wash solutions or solvents pick up relatively small amounts of solutes. Thus, these DNA and protein synthesis techniques generate outflows which, if collected separately, are relatively close to the starting input solutions and may be used again as is or with only minimal processing.

Synthesis of DNA commonly uses the phosphoramidite method which combines phosphoramidite building blocks in the presence of a tetrazole catalyst. Nucleoside phosphoramidites are derivatives of natural or synthetic nucleosides. A phosphoramidite is a normal nucleotide with protecting groups, such as a trityl group, added to its reactive amine, hydroxyl, and phosphate groups. These protecting groups prevent unwanted side reactions and force the formation of the desired product during synthesis. Synthesis begins with a single phosphoramidite tethered to a solid support by a linker such as a succinyl linker coupled to a long chain alkylamine spacer.

The phosphoramidite method uses a cycle of four different chemistry mixtures to add each individual nucleoside in a 3' to 5' synthesis direction. First, a dimethoxytrityl (DMT)-protected nucleoside phosphoramidite is deprotected by removal of the DMT using trichloroacetic acid (TCA) in a deblocking step. This reveals a free 5'-hydroxyl group. Second, in an activation step, a new DMT-protected phosphoramidite is coupled to the 5'-hydroxyl group of the growing oligonucleotide chain to form a phosphite triester. Third, a capping step acetylates any remaining unreacted 5' hydroxyl groups, making the unreacted oligonucleotide chains inert to further nucleoside additions and preventing one source of base deletions. Capping is accomplished by adding an acetylating reagent composed of acetic anhydride and N-methyl imidazole. This reagent reacts only with free hydroxyl groups to irreversibly cap the oligonucleotides in which coupling failed. Fourth, iodine oxidation converts the phosphite to a phosphate, producing a cyanoethyl-protected phosphate backbone stabilizing the phosphate linkage between the monomers in the growing oligonucleotide chain. The DMT protecting group is removed to allow the cycle to continue and add the next nucleoside.

The protection of the exocyclic amino groups on adenine, cytosine, and guanine is orthogonal to that of the 5'-hydroxy group because the DMT is removed at the end of each synthetic cycle. One technique is to use base-labile protecting groups on the exocyclic amino groups to create orthogonality with the TCA cleavage of the DMT protecting group.

DNA may also be synthesized by enzymatic techniques. Enzymatic synthesis of DNA uses a template-independent DNA polymerase, terminal deoxynucleotidyl transferase (TdT), which is a protein that evolved to rapidly catalyze the linkage of naturally occurring dNTPs. TdT adds nucleotides indiscriminately so it is stopped from continuing unregulated synthesis by various techniques such a tethering the TDT, creating variant enzymes, and using nucleotides that include reversible terminators to prevent chain elongation. TdT activity is maximized at approximately 37° C. and performs enzymatic reactions in an aqueous environment.

Techniques that use reversible terminators flood a reaction tube with only one type of deoxynucleotide triphosphates at a time (dNTPs). The reversible terminator prevents chain elongation so only a single nucleotide is added to the growing DNA strands. Once coupling has taken place, the free dNTPs are washed away, the terminator is removed with a deblocking solution, and the system is primed for the next round of single-nucleotide addition. Enzymatic synthesis may potentially create longer oligonucleotides than the phosphoramidite method and do so using water as the solvent thus reducing the toxic waste stream. Details of one technique for enzymatic synthesis of oligonucleotides are provided in U.S. Pat. No. 10,059,929.

Solid-phase synthesis of peptides (SPPS) is a technique commonly used to synthesize proteins. Peptide synthesis is the production of peptides, also referred to as polypeptides or proteins, where multiple amino acids are linked via amide bonds also known as peptide bonds. Peptides are chemically synthesized by the condensation reaction of the carboxyl group of one amino acid to the amino group of another. Protecting group strategies are usually necessary to prevent undesirable side reactions with the various amino acid side chains. Chemical peptide synthesis most commonly starts at the carboxyl end of the peptide (C-terminus) and proceeds toward the amino-terminus (N-terminus).

SPPS allows the rapid assembly of a peptide chain through successive reactions of amino acid derivatives on an insoluble porous support. The general SPPS procedure is one of repeated cycles of alternate N-terminal deprotection and coupling reactions. First, an amino acid is linked to the solid support with a covalent bond between the carbonyl group of the amino acid and solid support. The bond coupling the amino acid to the solid support may be an amido or an ester bond. Subsequently, the amine is deprotected and then coupled with the free acid of the second amino acid. This cycle repeats until the desired sequence has been synthesized. SPPS cycles may also include capping steps which block the ends of unreacted amino acids from reacting. The protecting groups for the amino groups used in peptide synthesis are fluorenylmethyloxycarbonyl group (Fmoc) and tert-butyloxycarbonyl (Boc). Reactive side chains of amino acids are also protected with protecting groups that are orthogonal to the protecting group used for the amino group.

Figure 1:
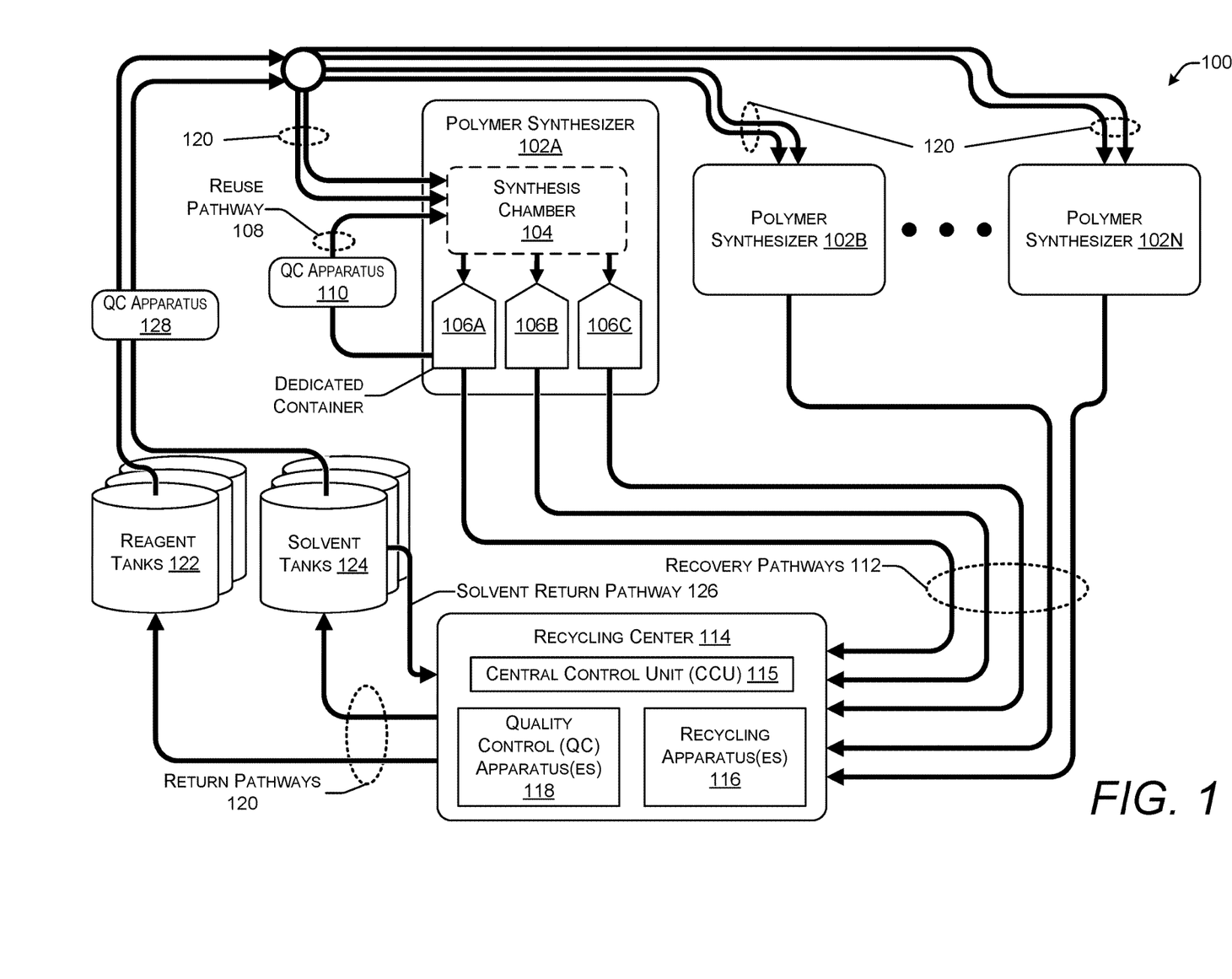
FIG. 1 is a fluid path diagram showing pathways between components of a system for synthesizing polymers.

FIG. 1 shows a fluid path diagram of a system 100 for synthesizing polymers. The polymers synthesized in this system may be synthesized using any of the techniques described above. The system 100 may include a plurality of polymer synthesizers 102A, 102B, . . . , 102N. The polymer synthesizers 102 may be oligonucleotide synthesizers, automated protein synthesizers, or another type of polymer synthesizer. Moreover, each of the individual polymers synthesizers 102A, 102B, . . . , 102N need not be the same model of machine or operate using identical hardware, reagent volumes, or timescales.

A first one of the polymer synthesizers 102A is shown in greater detail. This polymer synthesizer 102A is shown containing a synthesis chamber 104 and a plurality of dedicated containers 106A, 106B, and 106C for collecting outflow. Although not illustrated, the other polymer synthesizers 102B, . . . , 102N also include a synthesis chamber and dedicated containers for collecting outflow.

The synthesis chamber 104 is the portion of the polymer synthesizer 102 in which polymer synthesis occurs. The synthesis chamber 104 may include one or more solid supports upon which the polymers are synthesized. For example, the synthesis chamber 104 may include a flow cell, a column filled with beads, or a two-dimensional substrate such as a silicon chip. Solutions containing reagents, washes, and solvents may be flowed into the synthesis chamber 104 in a specific sequence according to the particular technique and chemistry used for polymer synthesis. Solutions added to the synthesis chamber 104 generally fill the synthesis chamber 104 and are present for a period of time sufficient to allow chemical or enzymatic reactions to occur. Depending on the configuration of the synthesis chamber 104, material inside may flow out due to gravity or may be mechanically removed such as by application of a vacuum or pump.

Addition of material to the synthesis chamber 104 is regulated by one or more inputs. The inputs may be implemented as valves or other devices for controlling the flow of fluids into the synthesis chamber 104. Material leaving the synthesis chamber 104 is referred to as "outflow" which is collected in one of multiple dedicated containers 106.

Each of the dedicated containers 106A, 106B, and 106C, may be associated with or "dedicated to" collecting outflow from a particular step of polymer synthesis. Thus, rather than collecting all the outflow from the synthesis chamber 104 as a single undifferentiated waste stream in a waste container, different containers are used to collect different types of outflow. The dedicated containers 106 may be constructed and connected to the synthesis chamber 104 in a way that is the same or similar to conventional waste containers. For example, the dedicated containers 106 may be plastic receptacles that are removably attached to an output from the synthesis chamber 104.

For example, outflow from a first step of synthesis that adds a first kind of monomer subunit may be collected in a first dedicated container 106A. Outflow from a second step of synthesis that adds a second kind of monomer subunit may be collected in a second dedicated container 106B. Outflow from a wash step that adds a wash solution which is primarily solvent may be collected in a third dedicated container 106C. Thus, after synthesis run there will be a first dedicated container 106A containing the first reagent which is the first type of monomer subunit, a second dedicated container 106B contain a second reagent which is the second type of monomer subunit, and a third dedicated container 106C containing a solution that is mostly solvent.

Although only three different dedicated containers 106A, 106B, and 106C are shown, the polymer synthesizer 102 may have any number of different dedicated containers 106. Moreover, the polymer synthesizers 102A, 102B, . . . , 102N may each have a different number of dedicated containers 106. There may be one dedicated container 106 for each step of polymer synthesis or for each type of unique outflow generated during polymer synthesis. For example, if there are two washing steps with the same wash solution, outflow from both steps may be collected in the same dedicated container 106.

The outflow from the synthesis chamber 104 may be routed to one of the dedicated containers 106A, 106B, or 106C by a routing mechanism that changes the flow of material leaving the synthesis chamber 104 and directs it to one or another of the dedicated containers 106. The routing mechanism may switch the routing of outflow from the synthesis chamber 104 to the second dedicated container 106B instead of the first dedicated container 106A when the inputs to the synthesis chamber 104 are changed. The switch may also be delayed by a period of time approximately equal to the length of time needed for fluid to flow through the synthesis chamber 104. Delaying the rerouting of the outflow may keep the collection of material leaving the synthesis chamber 104 in phase with the material entering. This can reduce the mixing of reagents or solvents from different steps of synthesis.

The routing mechanism may be implemented as a mechanism for controlling or changing the routing of fluids. Many types of fluid handling systems are known to those of ordinary skill in the art. For example, the control mechanism may include one or more of a pump, a valve, and a flowmeter. The routing mechanism may be a part of the polymer synthesizer 102 and may be added to an existing polymer synthesizer 102 in place of a conventional connection to a waste tank.

The contents of one or more of the dedicated containers 106A, 106B, and 106C may be reused by routing along a reuse pathway 108 that returns the contents of the dedicated container 106 to the input or to a feed container of the synthesis chamber 104. The feed container, not shown, is a container that holds a reagent or solvent prior to introducing that reagent or solvent into the synthesis chamber 104. Each reagent and or solvent used for polymer synthesis may be stored in a separate feed container. All of the feed containers may share the same input to the synthesis chamber 104 or individual ones are the be containers may have separate inputs. If the feed containers share the same input, a control mechanism may be used to regulate which feed container is connected to the synthesis chamber 104.

The reuse pathway 108 may be a fluid pathway that includes piping, tubing, valves, pumps, flow meters, or other automatic fluid processing systems. The reuse pathway 108 may also include manual actions such as a user separating the dedicated container 106 from the polymer synthesizer 102 and pouring the contents into a feed container used for the same reagent or solvent. The reuse pathway 108 may combine outflow of the same solution from multiple different polymer synthesizers 102 into a single outflow holding chamber that combines outflows from the same synthesis step. For example, if polymer synthesizer 102A is generating an outflow that contains a G-amidite solution and polymer synthesizer 102B is also generating an outflow with the same G-amidite solution, then both of these outflows may be routed through the reuse pathway 108 to the same dedicated container 106, holding chamber, etc. The combined outflows may also be analyzed by the QC apparatus 110 as a batch before being returned to one or more of the polymer synthesizers 102.

The reuse pathway 108 may simply return the contents of the dedicated container 106 to an input of the synthesis chamber 104 for reuse in a later iteration of the same step of polymer synthesis. For example, if a wash solution is collected in the dedicated container 106B, the wash solution may be routed through the reuse pathway 108 and reintroduced to the synthesis chamber 104 during a subsequent washing step that uses the same wash solution.

However, there may be limits on the number of times that reagents or solvents can be reused without modification. A quality control (QC) apparatus 110 may analyze all or part of the contents of the dedicated container 106 as it moves through the reuse pathway 108. Rather than testing the entire volume, an aliquot or small portion the contents of the dedicated container 106 may be moved into contact with a sensing component of the QC apparatus 110 for testing. The QC apparatus 110 may measure concentration, purity, volume, pH, temperature, or any other characteristic of the outflow collected in the dedicated container 106. Analysis by the QC apparatus 110 may determine if the contents of the dedicated container 106 have the appropriate characteristics (e.g., reagent concentration, solvent purity, total volume, etc.) for reuse in polymer synthesis.

The QC apparatus 110 may be implemented as any type of apparatus or device for measuring the characteristic(s) on which quality standards are based. For example, the QC apparatus 110 may be a volumetric measure or a scale to determine if the volume of the contents of the dedicated container 106 are within a predetermined volume range. The QC apparatus 110 may also include spectrometers to measure the concentration of a reagent using ultraviolet (UV) spectroscopy, infrared (IR) spectroscopy, UV/IR spectroscopy, and Ultraviolet-visible (UV/viz) spectroscopy, or other spectroscopy technique. The QC apparatus 110 may also be a gas chromatography-mass spectrometer (GC/MS) that performs gas chromatography-mass spectrometry or a liquid chromatography-mass spectrometer (LC-MS) that combines the physical separation capabilities of liquid chromatography (or HPLC) with the mass analysis capabilities of mass spectrometry (MS). Another type of QC apparatus 110 is a spectrophotometer which can also measure concentrations of reagents in solution. One example of a spectrophotometer is the NanoDrop™ line of spectrophotometers available from Thermo Fisher Scientific. The QC apparatus 110 may also be implemented as a pH measurement device such as a pH electrode which can determine if the pH of the contents of the dedicated container 106 is within a predetermined range.

The QC apparatus 110 may analyze the contents of the dedicated container 106 to determine if the outflow in the dedicated container 106 has the appropriate characteristics (e.g., concentration, purity, volume, etc.) for reuse. Depending on the results of the QC analysis, the contents of the dedicated container 106 may be routed through the reuse pathway 108 or through a recovery pathway 112.

In some implementations, outflows from the synthesis chamber 104 collected in one of the dedicated containers 106A, 106B, and 106C may be routed along recovery pathways 112 without QC analysis. For example, one of the dedicated containers 106 may be used to collect outflow that contains a mixture of reagents. Because there is a mixture of reagents, this outflow may not be suitable for reuse, so the contents of the dedicated container 106 would always be routed along one of the recovery pathways 112.

The recovery pathways 112 lead from the dedicated containers 106 in the polymer synthesizers 102 to the recycling center 114. The recovery pathways 112 may be implemented as piping, tubing, valves, pumps, flow meters, or other automatic fluid processing systems that move the contents of one or more of the dedicated containers 106A, 106B, and 106C to the recycling center 114. The recovery pathways 112 may also include one or more manual steps such as a user carrying a dedicated container 106 to the recycling center 114 and placing the contents in a recycling apparatus 116. Thus, the recovery pathways 112 may include automatic and/or manual techniques for moving fluids from the polymer synthesizer 102 to the recycling center 114.

The recycling center 114 may be at a central location, or portions of the recycling center 114 may be split across multiple different locations, serving one or more polymer synthesizer 102. Thus, in this system 100 there may be continual movement of reagent and solvent flow between various polymer synthesizers 102 and recycling apparatus 116 in the recycling center 114. The recycling apparatuses 116 are equipment or systems that are capable of cleaning, filtering, purifying, concentrating, diluting, adding reagents, or performing other manipulations to the contents of the dedicated containers 106. One function a recycling apparatus 116 may perform is to adjust the effective concentration of the reagent or the solvent in the outflow.

One type of recycling apparatus 116 is a still that can be used to distill and purify solvent from outflow that contains the solvent and solutes or other impurities. Material that remains in a still after distillation may be discarded as waste. For example, the solvent acetonitrile used with phosphoramidite synthesis may be recovered by distillation. However, if water is present in the solution acetonitrile forms a low-boiling azeotrope which is composed of 86% acetonitrile and 14% water. Therefore, recovery of acetonitrile may be performed using a high-efficiency fractional distillation system to remove the water and solutes from the acetonitrile. An acetonitrile-water azeotrope may also be purified by flowing the mixture over a bed of hygroscopic material that absorbs water followed by distillation.

Another type of distillation that may be performed by one of the recycling apparatuses 116 is vacuum distillation. Distillation performed under vacuum lowers the boiling point of the solvent and allows for distillation to be performed at lower temperatures than atmospheric pressure distillation. Distilling under vacuum may protect reagents such as enzymes that are sensitive to high heat and may also reduce energy consumption needed to heat the still. Distilling water from an enzyme solution may be used to increase the concentration of enzymes as well as to recover water for use as a solvent.

Another example of a recycling apparatus 116 is a flow-through membrane. A flow-through membrane can be used to perform dialysis and separate water from solutes. This may purify the water so that it can be used again as a solvent. Dialysis may also be used to concentrate solutions of enzymes by removing water while retaining the enzymes.

Additionally, the recycling apparatus 116 may be a liquid chromatography column which is able to separate substances based on differential adsorption of compounds to the adsorbent; compounds move through the column at different rates, allowing them to be separated into fractions. A liquid chromatography column may filter enzymes from solution and be used to elute the enzymes in a smaller volume thereby increasing the effective concentration.

A further example of the recycling apparatus 116 is a centrifuge that may be combined with filtration or purification columns to purify or remove components from a solution. A centrifuge works using the sedimentation principle, where the centrifugal acceleration causes denser substances and particles to move outward in the radial direction. At the same time, objects that are less dense are displaced and move to the center. In a laboratory centrifuge that uses sample tubes, the radial acceleration causes denser particles to settle to the bottom of the tube, while low-density substances rise to the top.

Another type of recycling apparatus 116 that may be used for processes such as separation, absorption, stripping, and distillation, is a packed bed absorber. In chemical processing, a packed bed absorber is a hollow tube, pipe, or other vessel that is filled with a packing material. The packing can be randomly filled with small objects or it can be filled with a specifically designed structured packing. Packed beds may also contain catalyst particles or adsorbents such as zeolite pellets, granular activated carbon, etc. The purpose of a packed bed is typically to improve contact between two phases in a chemical or similar process. Packed beds can be used in a chemical reactor, a distillation process, a scrubber, or the like.

An automated, or manual, system that adds additional reagent is a further type of recycling apparatus 116. Addition of additional reagent may bring that effective concentration of a reagent such as a nucleoside monomer back up to a concentration level that is within a predefined concentration range. Many reagents such as amidites and enzymes are available in a powdered form that can be added to solution to increase the concentration of the reagent. Powdered reagents or reagents in a concentrated liquid form are referred to as "concentrated reagents." The quantity of concentrated reagent needed to raise the concentration of a solution to level within the predefined concentration range may be determined by measuring the concentration of the solution using techniques such as spectrometry.

A central control unit (CCU) 115 may control operation of the recycling center 114 including determination of how much additional reagent or solvent to add in order to achieve a given effective concentration. The CCU 115 may make determinations about volumes, weights, amounts, etc. of concentrated reagent, solvent, or other substance to add based in part on data obtained from one or more QC apparatuses 118 that may also be included in the recycling center 114. For inflows to the recycling center 114 for which there are multiple possible options to recycle or refurbish the material, the CCU 115 may include logic, algorithms, decision flow graphs, or other computer-implemented technique or determining which recycling method to use.

The CCU 115 may also be in communicative connection with the one or polymer synthesizers 102 and receive data regarding the volume of reagent and solvent available within each. Additionally, data indicating the amount of available reagent and solvent from other sources such as reagent tanks 122 and solvent tanks 124 may be available to the CCU 115. Thus, the CCU 115 may perform inventory management functions to maintain the availability of reagents and solvents for the polymer synthesizers 102. The CCU 115 may have the ability to control the reuse pathway 108, the recovery pathways 112, and return pathways 120 optimize the efficiency, cost savings, and availability of the reagents and solvents. For example, the CCU 115 may route a solution to the recycling center 114 rather than through the reuse pathway 108 if it is determined that is more economically efficient to capture the solvent from that solution rather than to reuse the reagents present in that solution.

Processing with a recycling apparatus 116 may be referred to as "reconditioning." Reagents and solvents that pass through the recycling center 114 and are restored to a concentration, purity, or other condition that is closer to the condition of new reagents or solvents than to the condition of reagents or solvents in the outflow from the synthesis chamber 104 a referred to as reconditioned reagents or reconditioned solvents. Alternatively, they may also be referred to as recovered reagents or recovered solvents. Reconditioned reagents and reconditioned solvents may not have concentrations, purities, or other characteristics that are exactly the same as new reagents or new solvents. However, reconditioned reagents and reconditioned solvents are functionally equivalent to new reagents or new solvents when used for polymer synthesis.

The QC apparatuses 118 located in the recycling center 114 may be similar or identical to the QC apparatus 110 used to evaluate the outflow in the reuse pathway 108. The QC apparatuses 118 may be implemented as any type of apparatus or device for measuring the characteristic or characteristics on which quality standards are based.

QC analysis with a QC apparatus 118 may be performed before and/or after processing with a recycling apparatus 116. The QC analysis may determine which type of reconditioning or recycling is needed. If performed after reconditioning, QC analysis may be used to determine if the concentration or other characteristic of a reconditioned reagent reconditioned solvent is within acceptable thresholds for use in polymer synthesis. Reconditioned reagents are solvents that do not pass the QC analysis may be reprocessed and tested again or they may be discarded as waste.

Return pathways 120 from the recycling center 114 may include reagent tanks 122 for separately storing the different types of reagents and solvent tanks 124 for separately storing different types of solvents. The various types of reconditioned reagents produced at the recycling center 114 may be stored temporarily in one of the reagent tanks 122 until needed by a polymer synthesizer 102. Some of the reagents may have a limited shelf life once in solution. However, in a high throughput synthesis facility with multiple polymer synthesizers drawing from the reagent tanks 122, the reconditioned reagents will likely be used well before the shelf life becomes an issue.

Any reconditioned solvents produced by the recycling center 114 may be stored in one of the solvent tanks 124 until needed for use by the polymer synthesizer 102. Reconditioned solvents may also be used by the recycling center 114 to dilute or increase the volume of reagents. Reconditioned solvents may be moved from one of the solvent tanks 124 back to the recycling center 114 through a solvent return pathway 126.

The return pathways 120 may connect to each of the polymer synthesizers 102A, 102B, . . . , 102N creating a loop that can capture that outflow from polymer synthesis and return it to an input for a synthesis chamber 104. Reconditioning may be performed at the recycling center 114 between synthesis runs or while one group was synthesizers 102 are actively synthesizing polymers. The reconditioned reagents and reconditioned solvents stored in the reagent tanks 122 and the solvent tanks 124 may be used by any of the synthesizers in the system 100. Recycling and reuse of reagents and solvents can greatly reduce but not eliminate the need for introducing new reagents and new solvents into the system 100.

The portion of the return pathways 120 between the reagent tanks 122, the solvent tanks 124 and the polymer synthesizers 102 may include an additional QC apparatus 128. This QC apparatus 128 may contain any of the types of devices or equipment described in conjunction with the other QC apparatuses 110 and 118. A QC analysis on the reagents and solvents prior to returning them to the polymer synthesizers 102 may perform an additional check on the concentration and purity of reagents and solvents as well as ensure that the reagents are mixed properly before entering one of the polymer synthesizers 102.

Figure 2:
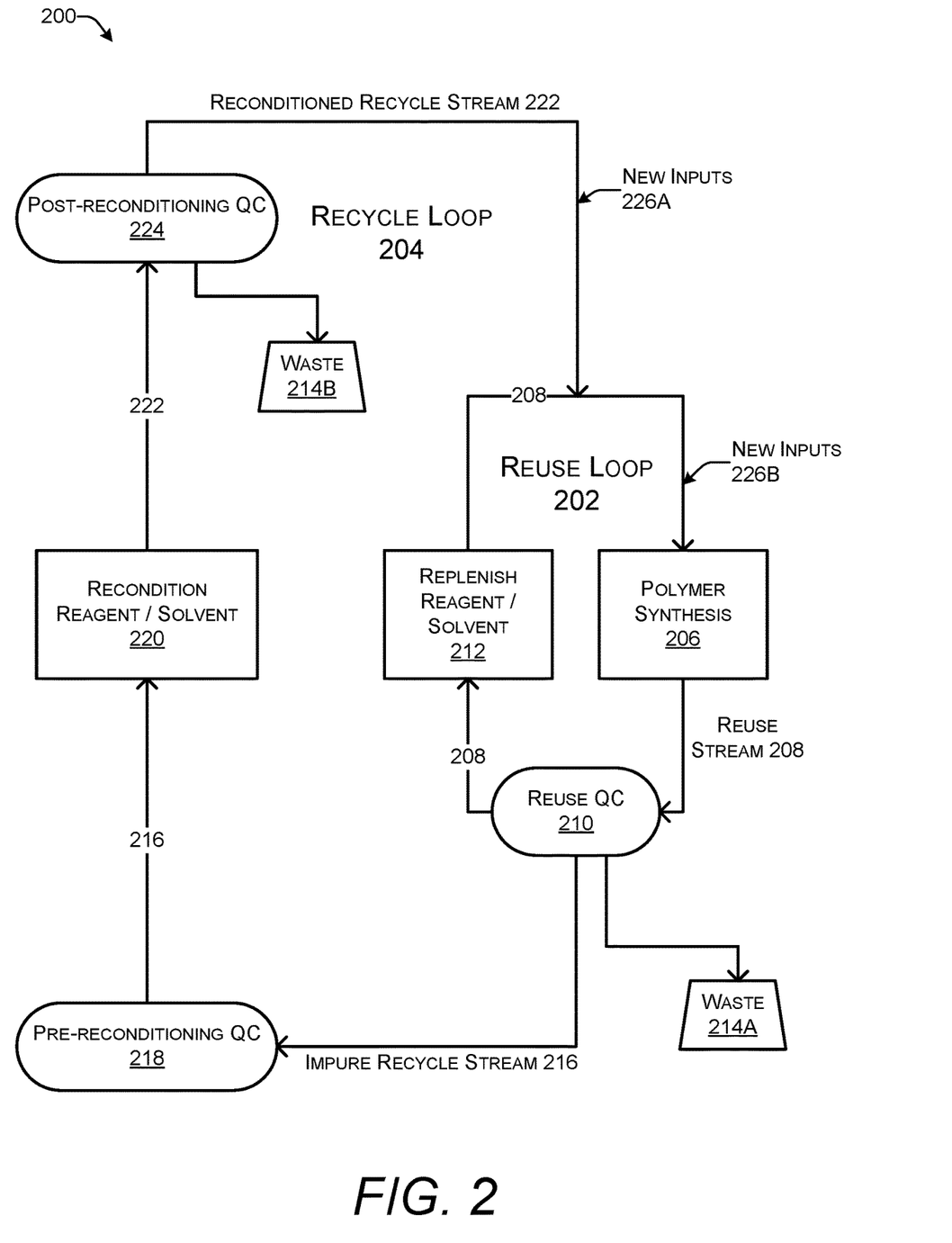
FIG. 2 is a process diagram showing a reuse loop and recycle loop for reagents and solvents used in polymer synthesis.

FIG. 2 is a process diagram 200 showing a reuse loop 202 and a recycle loop 204 indicating the movement of reagents and solvents through the system 100 shown in FIG. 1. The reuse loop 202 shows the reuse of reagents or solvents during polymer synthesis 206. The reuse loop 202 may operate during a single synthesis run so that reagents or solvents used during a step earlier in the synthesis run may be reused at a later step in the same synthesis run. The reuse stream 208 represents the flow of reagents and or solvents through the reuse loop 202. The reuse loop 202 may be associated with a single polymer synthesizer so the reuse stream 208 returns to the same polymer synthesizer from which it began. Thus, the reuse loop 202 can recirculate reagents and solvents multiple times through a polymer synthesizer.

The reuse loop 202 may include reuse QC 210 that can determine based on QC thresholds whether the reuse stream 208 is returned to the polymer synthesis 206, routed to the recycle loop 204, or directed to waste 214A. Some reagents and solvents may be able to be reused multiple times. In one implementation, reuse QC 210 may simply count the number of times that a given reagent or solvent has cycled through the reuse loop 202. After a predetermined number of times, reuse QC 210 may send the reagent or solvent to the recycle loop 204. Thus, QC analysis may be simply counting a number of reuse cycles. The number of cycles that a given reagent or solvent can be reused may be determined experimentally such as through trial and error. This number of acceptable reuse cycles may be a predetermined threshold that is set before synthesis begins. This is a measurement-free implementation in which the reuse loop 202 continues only for a set number of iterations and does not depend on a concentration, volume, or other measurement to determine if the reuse stream 208 is routed to the recycle loop 204.

In one implementation, reuse QC 210 may measure the volume outflow from polymer synthesis 206 or concentration of a reagent in the reuse stream 208. Measurement of volume or concentration may be performed by a QC apparatus 110 as shown in FIG. 1. If a QC measurement is within a predetermined threshold such as a concentration range or a volume range, then the reuse stream 208 may continue and return the reagent or solvent to polymer synthesis 206. If the QC measurement is outside of a predetermined range, then the contents of the reuse stream 208 may be replenished at 212 or routed to the recycle loop 204.

Replenishment of the reagent/solvent 212 includes addition of reagent or solvent to the reuse stream 208. Replenishment may occur relatively quickly through addition of powdered reagents or liquid solvent. This type of manipulation can adjust the effective concentration of a reagent or solvent in the reuse stream 208 within the timeframe available for a cycle through the reuse loop 202. For example, if analysis at reuse QC 210 determines that the volume is below a threshold, then replenishment 212 may add additional solvent to increase the volume. Similarly, if the measurement of reagent concentration at reuse QC 210 determines that the concentration of reagent is too low, additional concentrated reagent may be added as the replenishment 212.

Reagent such as nucleotide solutions are consumed during synthesis of polymers. Thus, the concentration of nucleotide solutions will gradually decrease as individual nucleotide monomers are pulled out of the solution and added to growing polymers during polymer synthesis 206. The nucleotide solutions may be refreshed by addition of additional nucleotides return the effective concentration back to the starting level.

Analysis performed during reuse QC 210 may also determine that the contents of the reuse stream 208 should be discarded in which case the reuse stream 208 is routed to a waste 214A. This may be the result of contamination or unintended mixing of outflows from different steps of polymer synthesis 206.

A stream of reagents or solvents routed from the reuse stream 208 to the recycle loop 204 may be referred to as an impure recycle stream 216. The impure recycle stream 216 contains reagents or solvents that did not meet the QC standards for reuse.

Contents of the impure recycle stream 216 may be evaluated by pre-reconditioning QC 218. The pre-reconditioning QC 218 may be performed by one of the QC apparatuses 118 shown in FIG. 1. The pre-reconditioning QC 218 may determine if and how to recondition a reagent. For example, the pre-reconditioning QC 218 may determine if a nucleotide solution should be processed to return the concentration of the nucleotides to within a threshold range or if the nucleotide solution should be processed to recover the solvent while discarding any remaining nucleotides.

Some types of impure recycle stream 216 contents in such as solvents may not be subjected to pre-reconditioning QC 218. Pre-reconditioning QC 218 may be omitted if, for example, the type of reconditioning and the way in which reconditioning is performed does not depend on the condition of the incoming material. For example, a solvent that will be recovered through distillation may be subject to the same distillation conditions regardless of the quantity of solutes or impurities in the solvent.

After the pre-reconditioning QC 218, if any, the impure recycle stream 216 is reconditioned 220. The reconditioning 220 may be performed by one of the recycling apparatuses 116 shown in FIG. 1. Reconditioning 220 of a reagent or solvent may include adjusting the effective concentration. The effective concentration may be adjusted by addition of reagents, removal of solution, purification, distillation, dialysis, or other manipulation. The reconditioning 220 may include filtering for all of the impure recycle stream 216 to remove solids. Solids may enter the impure recycle stream 216 through contamination, degradation of piping, material from valves, or other fluid processing apparatuses as well as from precipitation and crystallization of chemicals in reagents or solvents.

After being reconditioned at 220, the reagent or solvent may be referred to as a recondition recycle stream 222. The recondition recycle stream 222 includes reagent or solvent that has been reconditioned by processing in a way that adjusts the concentration of the reagent or solvent to within a predetermined threshold range of concentrations. Reconditioned reagents or reconditioned solvents may have characteristics such as a concentration or purity that are not necessarily identical to new reagent or new solvent but that will work in the same way as new reagent or new solvent for polymer synthesis. Thus, the recondition reagent or solvent may be used in place of new reagent for solvent or subsequent polymer synthesis 206.

Following reconditioning 220, there may be post-reconditioning QC 224. Analysis performed as part of post-reconditioning QC 224 may determine if the reconditioning 220 restored the effective concentration or purity of a reagent or solvent to within an appropriate range. Thus, the post-reconditioning QC 224 tests the effectiveness of the reconditioning 220. If the reconditioning 220 did not return the effective concentration of a reagent or solvent to a level that is within a predetermined threshold concentration, then the contents of the reconditioned recycle stream 222 may be returned to be reconditioned 220 once again or directed to waste 214B. Additionally, some products from the reconditioning 220 may be directly sent to the waste 214B such as the material remaining in a still after distillation of solvent.

Even though some materials such as solvents are not consumed during polymer synthesis 206, there may be loss through evaporation, disposal of contaminated or mixed reagents/solutions in waste 214, etc. Thus, both new inputs 226 of reagents and solvents may need to be added back into the recycle loop 204 or the reuse loop 202 from time to time. New inputs 226A added into the recycle loop 204 may be combined with reconditioned reagents or reconditioned solvents in the recondition recycle stream 222 or added separately to a polymer synthesizer. For example, periodically a polymer synthesizer may start a new synthesis run using entirely new reagents and new solvents. These new reagents and new solvents then enter that reuse loop 202 and subsequently the recycle loop 204.

New inputs 226B may also be added to the reuse loop 202. These new inputs 226B are not the concentrated reagents that may be added as part of replenishing a reagent 212 but are new reagent solutions or solvents added to the synthesis chamber of a polymer synthesizer during a synthesis run. For example, during a long synthesis run the solvent, even if some of the solvent is placed into the reuse stream 208 and reused, may eventually be fully consumed requiring the addition of new solvent.

Figure 3:
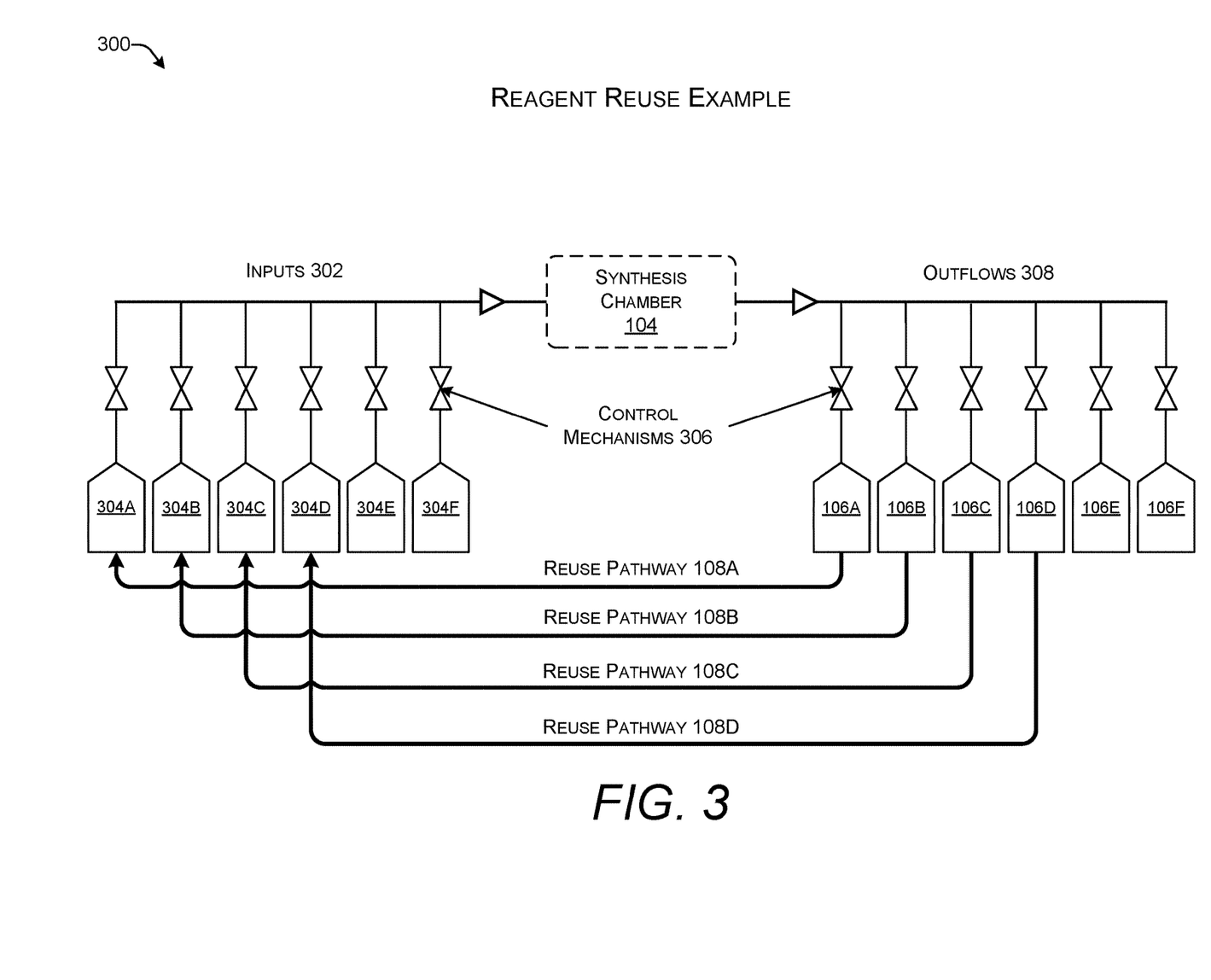
FIG. 3 shows a schematic view of a polymer synthesizer configured to reuse reagents.

FIG. 3 shows a schematic view 300 of a polymer synthesizer configured for reuse of reagents. For example, the reagents may be four different nucleoside mixtures (e.g., A, G, C, T) used for DNA synthesis. The nucleotide mixtures may be nucleoside phosphoramidites for phosphoramidite synthesis or dNTPs for enzymatic DNA synthesis.

The inputs 302 represent one or more openings, valves, tubes, connectors, etc. through which reagents and solvents that may be added to the synthesis chamber 104. Individual reagents or solvents may be provided from separate feed containers 304. In this example view 300, there are six different feed containers 304A, 304B, 304C, 304D, 304E, and 304F. However, there may be a greater or lesser number of feed containers 304. Control mechanisms 306 may control which of the feed containers 304 has a fluid connection with and provides its contents to the synthesis chamber 104 any given time. The control mechanisms 306 may be implemented as pumps, valves, or other fluid handling mechanism for regulating the inputs 302.

The feed containers 304A, 304B, 304C, and 304D may each contain a different nucleotide mixture (e.g., A, G, C, and T). For enzymatic DNA synthesis, the feed containers 304A, 304B, 304C, and 304D may be temperature regulated and maintained at a temperature that maximizes enzyme activity such as, for example, 37° C. the synthesis chamber 104 may also be temperature regulated for enzymatic DNA synthesis. Feed container 304E may contain a wash solution which may be made entirely or mostly of the solvent used for the nucleotide mixtures. For phosphoramidite synthesis, the wash solution may contain the solvent acetonitrile. For enzymatic DNA synthesis, the wash solution may contain the solvent water. The feed container 304F may contain a deblock solution that removes a reversible terminator or protecting group and allows addition of the next nucleoside.

Polymer synthesis may proceed using conventional techniques by adding the contents of the feed containers 304A, 304B, 304C, 304D, 304E, and 304F to the synthesis chamber 104 in an order specified by the synthetic technique. The outflows 308 from the synthesis chamber 104 are collected in multiple separate dedicated containers 106 rather than in a single waste container. In this example, there may be six dedicated containers 106A, 106B, 106C, 106D, 106E, and 106F corresponding to each of the feed containers 304A, 304B, 304C, 304D, 304E, and 304F. A routing mechanism may regulate operation of the control mechanisms 306 to direct outflows 308 from the synthesis chamber 104 into a specific one of the dedicated containers 106.

For enzymatic DNA synthesis, the enzymes and dNTP's collected in the dedicated containers 106A, 106B, 106C, and 106D may be reused. Because they will be reused potentially within a short timeframe, the dedicated containers 106A, 106B, 106C, and 106D may be temperature regulated to maintain the enzymes at a temperature that maximizes enzyme activity such as, for example, 37° C. or at lower temperatures such as, for example 17° C., for short-term storage as part of the recycling process. This is different from standard waste containers that are not temperature regulated.

Each of the nucleotide mixtures collected in the dedicated containers 106A, 106B, 106C, and 106D may be returned to the feed containers 304A, 304B, 304C, and 304D for the same nucleotide. Thus, the outflow that contains nucleotides with the base adenine is returned to the feed container 304A used to provide adenine to the synthesis chamber 104. The nucleotide mixtures are each returned to the respective feed containers 304A, 304B, 304C, and 304D by separate reuse pathways 108A, 108B, 108C, and 108D. The separate reuse pathways 108A, 108B, 108C, and 108D may be implemented using separate piping, tubing, pumps, or other fluid handling equipment.

The outflow of the nucleotide mixtures collected in the dedicated containers 106A, 106B, 106C, and 106D may be modified to obtain the same effective concentration of nucleotides as new nucleotide mixtures. If the effective concentration is too low, the effective concentration may be increased by addition of concentrated nucleotides. If the effective concentration is too high, the nucleotide mixtures may be diluted by addition of solvent. Adjusting the effective concentration of the nucleotides is an example of the replenish reagent step 212 shown in FIG. 2.

It may be possible for the nucleotide solutions to be reused a number of times (e.g. 1-5) before replenishment of nucleotides is necessary. Replenishment of nucleotides the addition of concentrated nucleotides may be continued for many further rounds of reuse. However, at some point contamination and impurities may increase such that the mixture collected in the dedicated containers 106A, 106B, 106C, and 106D is sent to a recycling step. The rate at which different nucleotides, or any reagent, is consumed may vary based on the specific polymers being synthesized. For example, synthesizing a set of DNA strands with a high GC content will consume nucleotides with guanine and cytosine bases faster than nucleotides adenine and thymine bases. Accordingly, guanine and cytosine nucleotide solutions may need to be refreshed more frequently than the adenine and thymine nucleoside solutions. Thus, each separate reagent may have its own timing of cycling through the reuse pathway 108 and eventually moving to the recycle pathway.

Figure 4:
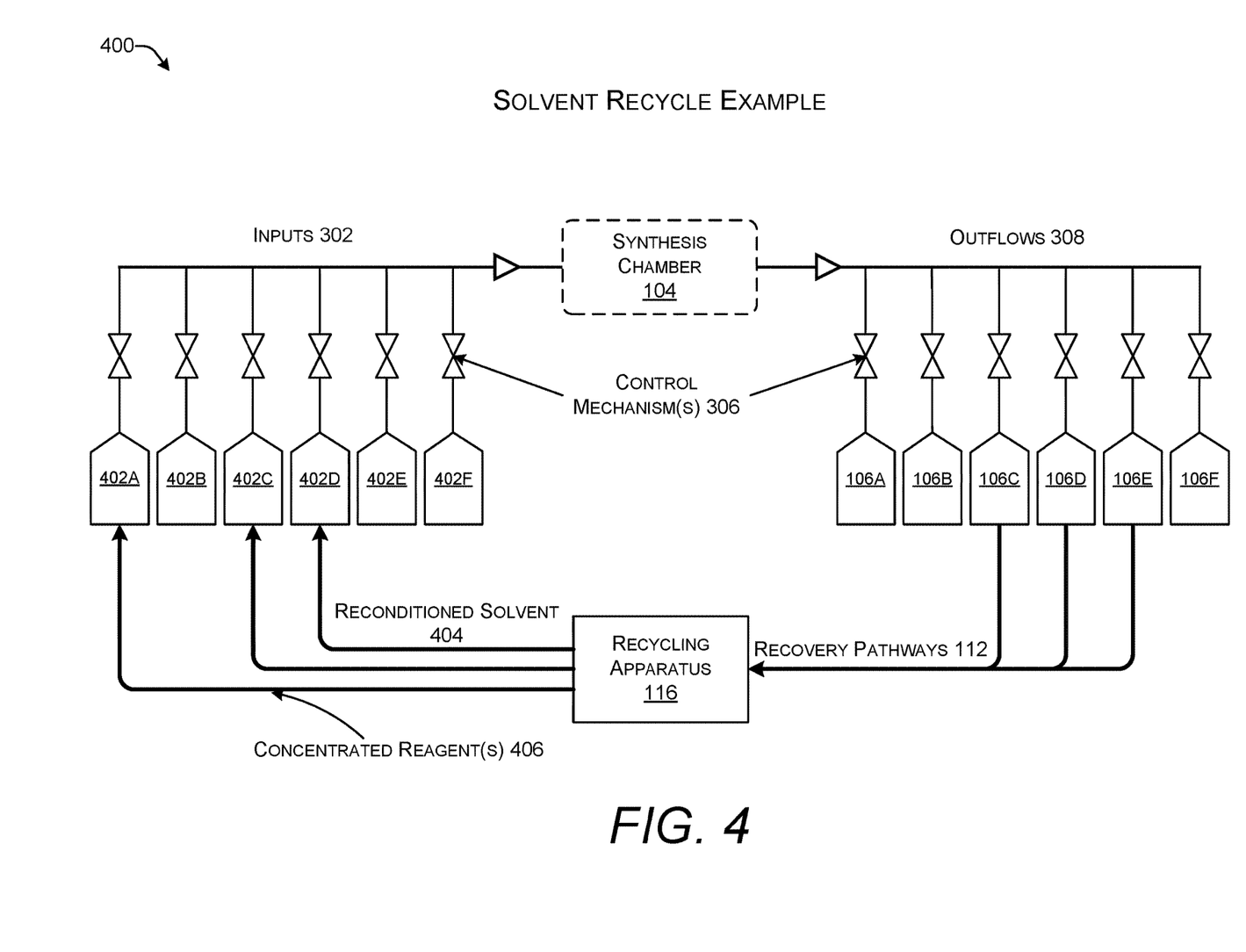
FIG. 4 shows a schematic view of a polymer synthesizer and associated recycling apparatus configured to recycle a solvent used in polymer synthesis.

FIG. 4 shows a schematic view 400 of a polymer synthesizer and recycling apparatus for recycling a solvent used in polymer synthesis. The solvent may be, for example, acetonitrile in the case of phosphoramidite synthesis or water in the case of enzymatic DNA synthesis.

The view 400 of the polymer synthesizer in FIG. 4 is similar to the view 300 shown in FIG. 3. The polymer synthesizer includes a plurality of inputs 302 connected to a synthesis chamber 104 which in turn is connected to a plurality of outflows 308. Multiple feed containers 402A, 402B, 402C, 402D, 402E, and 402F are connected to the inputs 302 and fluid connection between the feed containers 402 and the inputs 302 is regulated by control mechanisms 306. The outflows 308 are connected to multiple dedicated containers 106A, 106B, 106C, 106D, 106E, and 106F each dedicated to collecting outflow from respective one of the feed containers 402A, 402B, 402C, 402D, 402E, and 402F. By way of explanation, dedicated container 106A may be used to collect the outflow from feed container 402A. The correspondence between one of the feed containers 402 in one of the dedicated containers 106 may be maintained by coordinated operation of the control mechanisms 306.

In this example, dedicated containers 106C, 106D, and 106E, may each collect outflows 308 that are captured for the purpose of recycling the solvent. Each of the dedicated containers 106C, 106D, and 106E may collect different reagent or solvent outflows. The contents of these dedicated containers 106C, 106D, and 106E may be pooled and returned along recovery pathways 112 to a recycling apparatus 116. The recycling apparatus 116 is configured to recover solvent from solutions and may be, for example, a still used for distillation or a semi-permeable membrane use for dialysis.

Processing at the recycling apparatus 116 may generate reconditioned solvent 404 that can be returned to one or more of the feed containers such as feed containers 402C and 402D which may each contain different wash solutions that are primarily composed of solvent.

The reconditioned solvent 404 may also be mixed with concentrated reagents 406 to create a reagent solution such as an amidite solution that is placed in feed container 402A. Thus, the reconditioned solvent 404 generated by the recycling apparatus 116 may be directly added to feed containers 402C and 402D and also used as a diluent and mixed with a concentrated reagent 406 to create a reagent solution that is added to feed container 402A.

Illustrative Processes

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Figure 5:
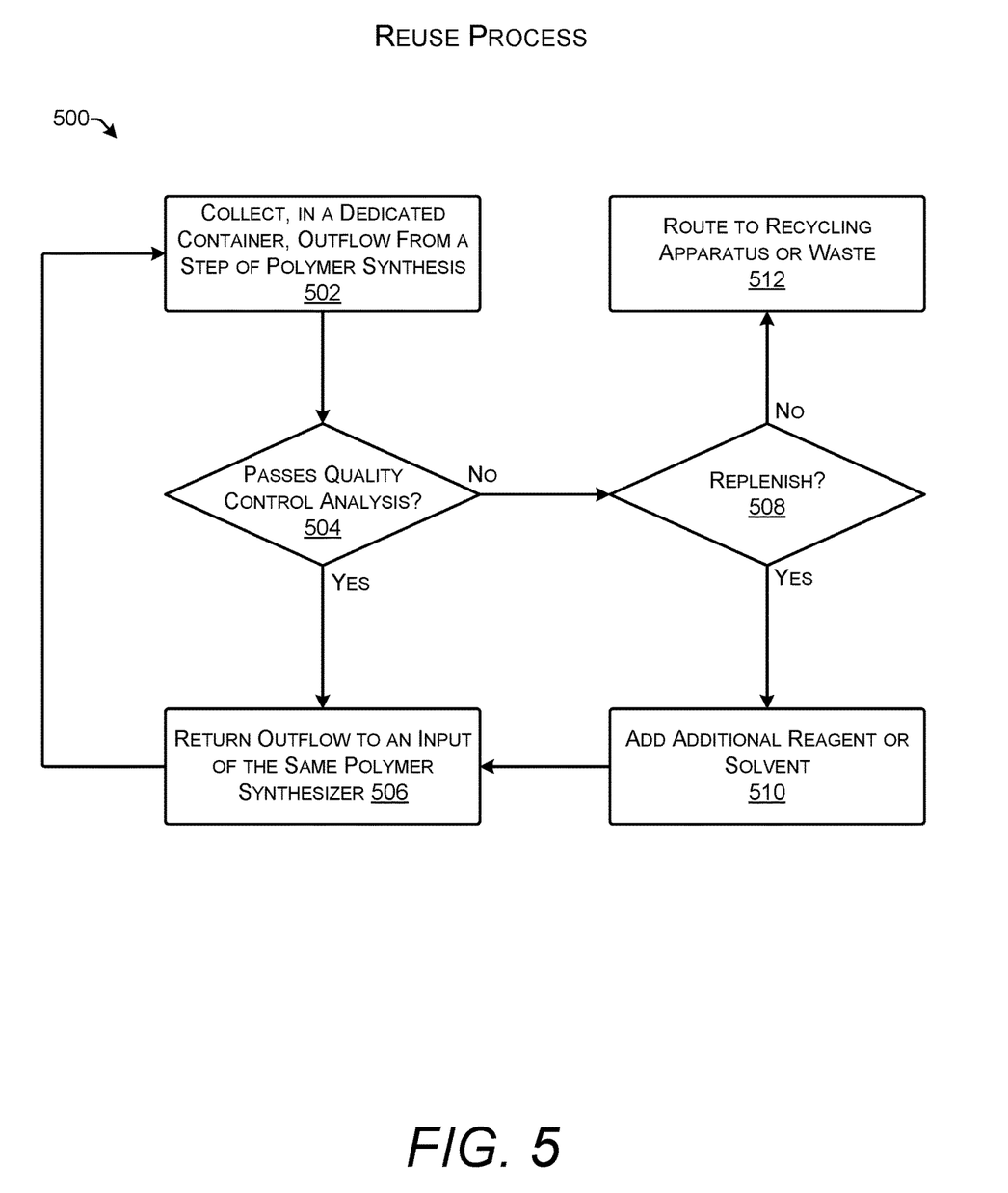
FIG. 5 is a flow diagram showing an illustrative process for reusing reagents or solvents during polymer synthesis.

FIG. 5 shows process 500 for using reagents or solvents during polymer synthesis. Process 500 may be implemented, for example, using any of the systems, devices, or apparatuses shown in FIGS. 1-4.

At 502, outflow of reagent or solvent from a step of polymer synthesis at a polymer synthesizer is collected in a dedicated container. The dedicated container may be one of multiple dedicated containers connected to the outflow from the polymer synthesizer such as the dedicated containers 106 shown in FIGS. 1, 3, and 4.

The polymer synthesizer may be an oligonucleotide synthesizer. The polymer synthesis may be, for example, phos-phoramidite-based synthesis of DNA in which the solvent is acetonitrile and the reagent may be a nucleoside phosphoramidite, an oxidizer, an activator, or a deblocker. Alternatively, the polymer synthesis may be enzymatic DNA synthesis using water as a solvent and the reagent may be the enzyme terminal deoxynucleotidyl transferase (TdT) or a deblocker.

At 504, QC analysis may be performed on the outflow. The QC analysis measures a characteristic of the outflow such as volume, effective concentration, or purity. The QC analysis may be performed by the QC apparatus 110 shown in FIG. 1. If the outflow collected in the dedicated container passes the QC analysis then process 500 proceeds along the yes path to 506.

At 506, responsive to determining that the outflow passes the QC analysis outflow is returned from the dedicated container to an input of a polymer synthesizer used to supply the reagent or the solvent. The outflow may be returned to the input of the polymer synthesizer via the reuse pathway 108 shown in FIG. 1. This is reuse of the reagent or solvent without modification or adjustment of the effective concentration. The reagent or solvent is used in the same polymer synthesizer for the same step of polymer synthesis. For example, if the reagent is a nucleotide solution containing nucleotide monomers with the base thymine, this reagent will be returned to an input of the polymer synthesizer during a subsequent thymine addition step.

The reagent or solvent that is returned to the input of the polymer synthesizer at 506 may again be collected in the outflow at 502. This represents one cycle of the reuse loop. The concentration purity, that the characteristics of a reagent or solid may change each time it is passed through the polymer synthesizer so that after a number of reuse cycles it no longer passes the quality control analysis at 504.

The quality control analysis may measure an effective concentration of a reagent in the outflow and determine that the outflow passes the QC analysis if the effective concentration of that reagent is within a predetermined concentration range. The predetermined concentration range may be different for each type of reagent and may be determined by the requirements of a given polymer synthesis technique. Effective concentration includes the amount of a reagent available to participate in chemical reactions and for enzymes such as TdT effective concentration also includes enzyme activity. Thus, in some implementations, QC analysis may measure enzyme activity which does not necessarily correlate with enzyme concentration.

QC analysis may also simply count the number of times that the contents of the dedicated container have been returned to the input of the polymer synthesizer. Thus, QC analysis may be implemented as a counter that increments each time process 500 proceeds through step 506 and returns outflow to the polymer synthesizer. If this number is less than a predetermined number, the QC analysis is satisfied. Once the predetermined number of reuse cycles has been exceeded, the outflow fails the QC analysis. The predetermined number may be identified by measuring the concentration of reagents during a testing phase to identify the number of cycles of use at which the concentration of the reagent drops below the minimum threshold level.

The QC analysis may also measure the purity or the number of contaminants in the outflow. If the purity is below a threshold level for the number of contaminants exceeds a threshold level then the outflow will fail the QC analysis. If the outflow fails the QC analysis for any of the above reasons, process 500 proceeds along the "no" path to 508.

At 508, is determined if the outflow collected in the dedicated container is replenished by addition of additional reagent or solvent. The decision to replenish the outflow may be based on results of the QC analysis. If the outflow is replenished at 508, process 500 proceeds along the "yes" path to 510. Replenishing the outflow by adding additional reagent or solvent modifies the effective concentration of the outflow so that it passes the QC analysis.

At 510, additional reagent or solvent is added. Additional reagent may be added as a concentrated reagent in powder form or as a concentrated liquid. Addition of concentrated reagent increases the effective concentration of the reagent in the outflow. Addition of solvent may increase volume without increasing the quantity of reagents thereby lowering the effective reagent concentration. Addition of solvent may also be used to increase the volume of the outflow.

If the outflow is not replenished at 508 because, for example, replenishment will not return the outflow to a condition suitable for reuse, process 500 proceeds along the "no" path to 512. At 512, the contents of the dedicated container are routed to a recycling apparatus or to waste. The determination to route the contents of the dedicated container to the recycling apparatus may be made at 504 in response determining that the outflow fails the QC analysis. The recycling apparatus may be one of the recycling apparatuses 116 shown in FIG. 1. Processing of outflow through recycling is described in FIG. 6.

Figure 6:
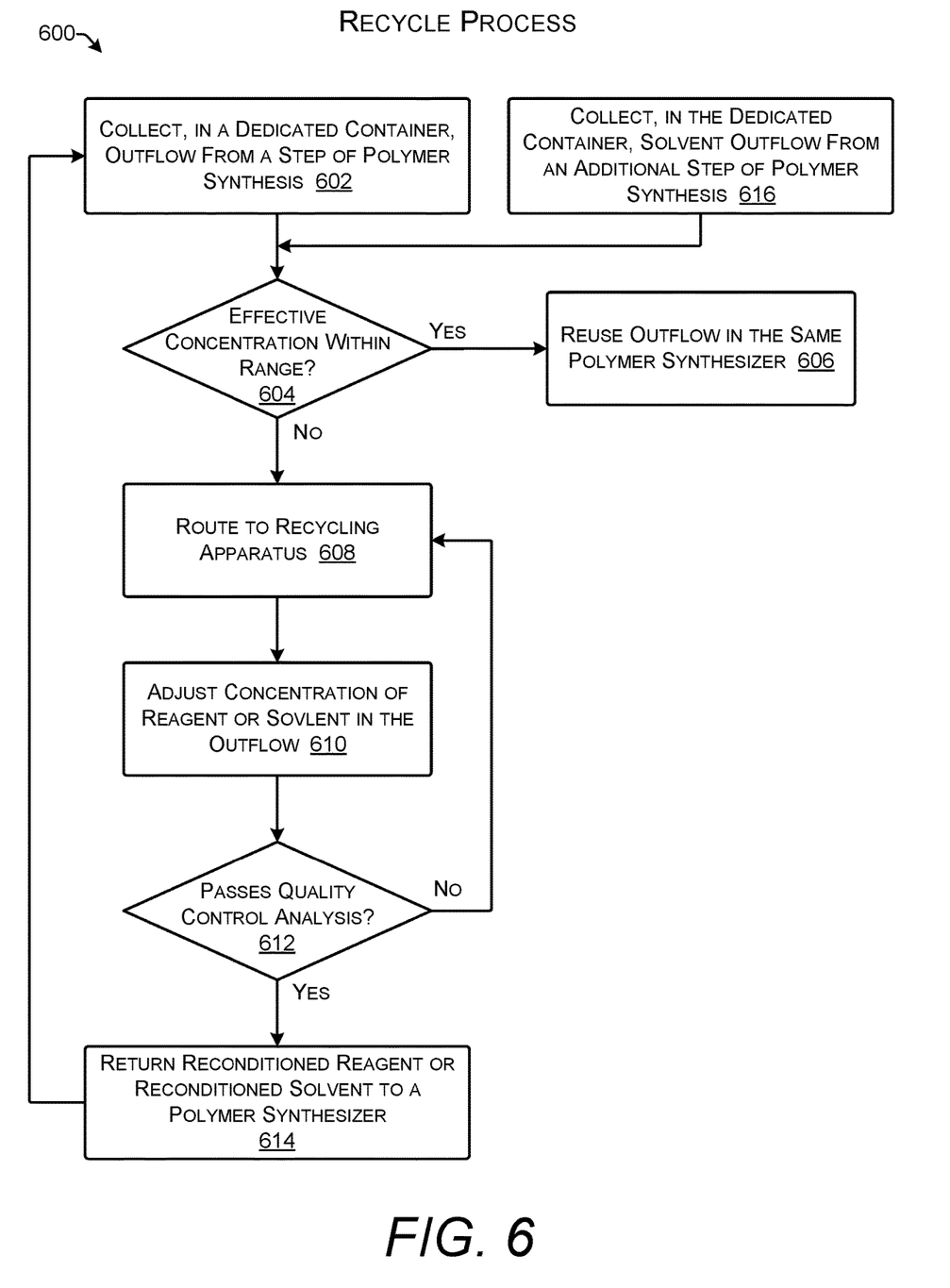
FIG. 6 is a flow diagram showing an illustrative process for recycling reagents or solvents used in polymer synthesis.

FIG. 6 shows process 600 for recycling reagents or solvents used in polymer synthesis. Process 600 may be implemented, for example, using any of the systems, devices, or apparatuses shown in FIGS. 1-4.

At 602, the outflow of a reagent or a solvent from a step of polymer synthesis is collected in a dedicated container. The dedicated container may be one of multiple dedicated containers connected to the outflow from the polymer synthesizer such as the dedicated containers 106 shown in FIGS. 1, 3, and 4.

The polymer synthesizer may be an oligonucleotide synthesizer. The polymer synthesis may be, for example, phosphoramidite-based synthesis of DNA in which the solvent is acetonitrile and the reagent may be a nucleoside phosphoramidite, an oxidizer, an activator, or a deblocker. Alternatively, the polymer synthesis may be enzymatic DNA synthesis using water as a solvent and the reagent may be the enzyme terminal deoxynucleotidyl transferase (TdT) or a deblocker.

At 604, is determined if the effective concentration of the reagent or solvent is within a predetermined concentration or purity range. The effective concentration may be the concentration of a reagent available for participation in chemical reactions or activity level of an enzyme. If the effective concentration is within the predetermined concentration range, then process 600 may proceed along the "yes" path to 606.

At 606, the outflow may be reused in the same polymer synthesizer. Reuse of outflow collected in a dedicated container is described in FIG. 5.

If however, the effective concentration of the outflow in the dedicated container is outside of the predetermined concentration range, process 600 proceeds are the "no" path from 604 to 608. At 608, the contents of the dedicated container are routed to a recycling apparatus. The recycling apparatus may be one of the recycling apparatuses 116 shown in FIG. 1. For example, the recycling apparatus may be a still, a semi-permeable membrane, a filtration column, a centrifuge, or a packed bed absorber.

At 610, the effective concentration of a reagent or solvent in the outflow is adjusted to create a reconditioned reagent or a reconditioned solvent. Adjusting effective concentration may include increasing the concentration or decreasing the concentration. Adjusting the effective concentration may include adding additional reagent to a solution containing some but less than a threshold concentration of the reagent. Adjusting the effective concentration of the solvent may include removing solutes from the solvent thereby increasing the purity and concentration of the remaining solvent.

At 612, is determined if the reconditioned reagent or the reconditioned solvent passes a QC analysis. The QC analysis may be performed by one of the QC apparatuses 118 shown in FIG. 1. If the reconditioned reagent or the reconditioned solvent does not pass the QC analysis, process 600 may proceed along the "no" path and return to 608 where the reconditioned reagent or reconditioned solvent is again routed to the recycling apparatus for repeat processing.

However, if the QC analysis at 612 following the reconditioning of the reagent or solvent indicates successful reconditioning, then process 600 proceeds along the "yes" path to 614. At 614, the reconditioned reagent or the reconditioned solvent is returned to an input of a polymer synthesizer. This may or may not be the same polymer synthesizer from which the outflow was originally collected. In some implementations, reconditioned solvents and reconditioned reagents from multiple different polymer synthesizers may be collected together in one or more reagent tanks 122 or solvent tanks 124 as shown in FIG. 1. The reconditioned reagent or reconditioned solvent may be returned via one of the return pathways 120 shown in FIG. 1.

The input of the polymer synthesizer is an input that supplies the same reagent or the same solvent for polymer synthesis. For example, if the solvent is water collected from enzymatic DNA synthesis, once reconditioned through distillation, dialysis, or other technique, the water can be returned to an input that is used for a water-wash step of polymer synthesis.

At 616, an additional outflow from an additional step of polymer synthesis may be collected in the same dedicated container used to collect the outflow at 602. For this path of process 600, the outflows collected at 602 and at 616 both contain the same solvent. These outflows are used for recovering the solvent so reagents or solutes in the outflows will be discarded. Therefore, any differences between the contents of outflows and any mixing will not affect the final ability to recover solvent from the combined outflows. This combined solvent outflow is processed through the remaining steps of process 600 as described above. In some implementations, multiple solvent outflows may be collected in different dedicated containers and combined at a later stage in process 600.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of reusing reagents and solvents during polymer synthesis (206), the method comprising: collecting, in a dedicated container (106), outflow of a reagent or a solvent from a step of polymer synthesis at a polymer synthesizer (102); performing quality control (QC) analysis (210) on the outflow; and responsive to determining that the outflow passes the QC analysis, returning the outflow from the dedicated container (106) to an input of the polymer synthesizer (102) used to supply the reagent or the solvent for the same step of polymer synthesis (206).

Clause 2. The method of clause 1, wherein the polymer synthesis is phosphoramidite-based synthesis of deoxyribonucleic acid (DNA) and the reagent comprises a nucleoside phosphoramidite, an oxidizer, an activator, or a deblocker or the solvent comprises acetonitrile.

Clause 3. The method of any of clauses 1-2, wherein the polymer synthesis is enzymatic DNA synthesis and the reagent comprises terminal deoxynucleotidyl transferase (TdT) or a deblocker or the solvent comprises water.

Clause 4. The method of any of clauses 1-3, wherein the QC analysis comprises measuring an effective concentration of the reagent in the outflow and determining that the outflow passes the QC analysis comprises determining that the effective concentration of the reagent is within a predetermined concentration range.

Clause 5. The method of any of clauses 1-4, wherein the QC analysis comprises counting a number of times contents of the dedicated container have been returned to the input of the polymer synthesizer and determining that the outflow passes the QC analysis comprises determining that the number of times is less than a predetermined number.

Clause 6. The method of any of clauses 1-5, further comprising responsive to determining that the outflow fails the QC analysis, adding additional reagent or solvent to the outflow.

Clause 7. The method of any of clauses 1-6, further comprising responsive to determining that the outflow fails the QC analysis, routing contents of the dedicated container to a recycling apparatus.

Clause 8. A method of recycling reagents and solvents for polymer synthesis (206), the method comprising: collecting, in a dedicated container (106), outflow of a reagent or a solvent from a step of polymer synthesis (206); routing contents of the dedicated container (106) to a recycling apparatus (116); adjusting an effective concentration of a reagent or solvent in the outflow to create a reconditioned reagent or a reconditioned solvent (222); and returning the reconditioned reagent or the reconditioned solvent (222) to an input of a polymer synthesizer (102) used to supply the reagent or solvent for polymer synthesis (206).

Clause 9. The method of clause 8, wherein the recycling apparatus comprises a new, a semi-permeable membrane, a filtration column, a centrifuge, or a packed bed absorber.

Clause 10. The method of any of clauses 8-9, wherein the effective concentration comprises a concentration of a reagent available for participation in chemical reactions or an activity level of an enzyme.

Clause 11. The method of any of clauses 8-10, wherein the adjusting the effective concentration comprises adding additional reagent to a solution containing the reagent.

Clause 12. The method of any of clauses 8-11, wherein the adjusting the effective concentration of the solvent comprises removing solutes from the solvent.

Clause 13. The method of any of clauses 8-12, further comprising determining an effective concentration of the reagent or the solvent after collection of the outflow in the dedicated container and wherein routing contents of the dedicated container to the recycling apparatus is responsive to the effective concentration of the reagent or the solvent being outside of a predetermined concentration range.

Clause 14. The method of any of clauses 8-13, further comprising determining that the reconditioned reagent or the reconditioned solvent passes a quality control (QC) analysis and wherein the returning the reconditioned reagent or the reconditioned solvent to the polymer synthesizer is responsive to the reconditioned reagent or the reconditioned solvent passing the QC analysis.

Clause 15. The method of any of clauses 8-14, wherein the outflow comprises a solvent and further comprising collecting, in the dedicated container, additional outflow from an additional step of polymer synthesis also comprising the solvent.

Clause 16. A system (100) for efficient use of reagents and solvents in polymer synthesis (206), the system comprising: a first polymer synthesizer (102A) comprising a first dedicated container (106A) for collecting outflow of a reagent or a solvent from a first step of polymer synthesis; a recycling center (114) comprising a recycling apparatus (116) configured to receive contents of the first dedicated container (106A) and adjust an effective concentration of the reagent or the solvent in the outflow to create a reconditioned reagent or a reconditioned solvent; and a return pathway configured to direct the reconditioned reagent or the reconditioned solvent to the first polymer synthesizer or to a second polymer synthesizer.

Clause 17. The system of clause 16, wherein the first polymer synthesizer further comprises: a second dedicated container for collecting outflow of a second reagent or the solvent from a second step of polymer synthesis; and a routing mechanism that directs the outflow from the first step of polymer synthesis to the first dedicated container and directs the outflow from the second step of polymer synthesis to the second dedicated container.

Clause 18. The system of any of clauses 16-18, wherein the first polymer synthesizer further comprises a reuse pathway that returns the contents of the first dedicated container to an input of the first polymer synthesizer used to supply the reagent or the solvent for the first step of polymer synthesis.

Clause 19. The system of clause 18, further comprising a quality control (QC) apparatus configured to determine if the contents of the first dedicated container pass a QC analysis and responsive determining that the contents of the first dedicated container pass the QC analysis, route the contents of the first dedicated container to the reuse pathway.

Clause 20. The system of clauses 16-19, wherein the recycling center further comprises a QC apparatus configured to determine if an effective concentration of the reconditioned reagent or the reconditioned solvent is within a predetermined concentration range.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of reusing reagents and solvents during polymer synthesis, the method comprising:
   collecting, in a dedicated container, outflow of a reagent or a solvent from a step of polymer synthesis at a polymer synthesizer;
   performing quality control (QC) analysis on the outflow; and
   responsive to determining that the outflow passes the QC analysis, returning the outflow without modification from the dedicated container to an input of the polymer synthesizer used to supply the reagent or the solvent for the same step of polymer synthesis.

2. The method of claim 1, wherein the polymer synthesis is phosphoramidite-based synthesis of deoxyribonucleic acid (DNA) and the reagent comprises a nucleoside phosphoramidite, an oxidizer, an activator, or a deblocker or the solvent comprises acetonitrile.

3. The method of claim 1, wherein the polymer synthesis is enzymatic DNA synthesis and the reagent comprises terminal deoxynucleotidyl transferase (TdT) or a deblocker or the solvent comprises water.

4. The method of claim 1, wherein the QC analysis comprises measuring an effective concentration of the reagent in the outflow and determining that the outflow passes the QC analysis comprises determining that the effective concentration of the reagent is within a predetermined concentration range.

5. The method of claim 1, wherein the QC analysis comprises counting a number of times contents of the dedicated container have been returned to the input of the polymer synthesizer and determining that the outflow passes the QC analysis comprises determining that the number of times is less than a predetermined number.

6. The method of claim 1, further comprising responsive to determining that the outflow fails the QC analysis, adding additional reagent or solvent to the outflow.

7. The method of claim 1, further comprising responsive to determining that the outflow fails the QC analysis, routing contents of the dedicated container to a recycling apparatus.

8. A method of recycling reagents and solvents for polymer synthesis, the method comprising:
   collecting, in a dedicated container, outflow of a reagent or a solvent from a step of polymer synthesis;
   routing contents of the dedicated container to a recycling apparatus;
   adjusting an effective concentration of a reagent or solvent in the outflow to create a reconditioned reagent or a reconditioned solvent, wherein adjusting the effective concentration comprises adding additional reagent to a solution containing the reagent or removing solutes from the solvent; and
   returning the reconditioned reagent or the reconditioned solvent to an input of a polymer synthesizer used to supply the reagent or solvent for polymer synthesis.

9. The method of claim 8, wherein the recycling apparatus comprises a new, a semi-permeable membrane, a filtration column, a centrifuge, or a packed bed absorber.

10. The method of claim 8, wherein the effective concentration comprises a concentration of a reagent available for participation in chemical reactions or an activity level of an enzyme.

11. The method of claim 8, further comprising determining an effective concentration of the reagent or the solvent after collection of the outflow in the dedicated container and wherein routing contents of the dedicated container to the recycling apparatus is responsive to the effective concentration of the reagent or the solvent being outside of a predetermined concentration range.

12. The method of claim 8, further comprising determining that the reconditioned reagent or the reconditioned solvent passes a quality control (QC) analysis and wherein the returning the reconditioned reagent or the reconditioned solvent to the polymer synthesizer is responsive to the reconditioned reagent or the reconditioned solvent passing the QC analysis.

13. The method of claim 8, wherein the outflow comprises a solvent and further comprising collecting, in the dedicated container, additional outflow from an additional step of polymer synthesis also comprising the solvent.

14. A system for efficient use of reagents and solvents in polymer synthesis, the system comprising:
   a first polymer synthesizer comprising a first dedicated container for collecting outflow of a reagent or a solvent from a first step of polymer synthesis, a second dedicated container for collecting outflow of a second reagent or the solvent from a second step of polymer synthesis, and a routing mechanism that directs the outflow from the first step of polymer synthesis to the first dedicated container and directs the outflow from the second step of polymer synthesis to the second dedicated container;
   a recycling center comprising a recycling apparatus configured to receive contents of the first dedicated container and adjust an effective concentration of the reagent or the solvent in the outflow to create a reconditioned reagent or a reconditioned solvent;

and
a return pathway configured to direct the reconditioned reagent or the reconditioned solvent to the first polymer synthesizer or to a second polymer synthesizer.

15. The system of claim 14, wherein the first polymer synthesizer further comprises a reuse pathway that returns the contents of the first dedicated container to an input of the first polymer synthesizer used to supply the reagent or the solvent for the first step of polymer synthesis.

16. The system of claim 15, further comprising a quality control (QC) apparatus configured to determine if the contents of the first dedicated container pass a QC analysis and responsive determining that the contents of the first dedicated container pass the QC analysis, route the contents of the first dedicated container to the reuse pathway.

17. The system of claim 14, wherein the recycling center further comprises a QC apparatus configured to determine if an effective concentration of the reconditioned reagent or the reconditioned solvent is within a predetermined concentration range.

18. The system of claim 14, further comprising a central control unit (CCU) configured to determine an amount of additional reagent or an amount of additional solvent to add to the first dedicated container to achieve the effective concentration.

19. The system of claim 14, wherein the recycling apparatus is one or more of a still, a vacuum still, a flow-through membrane, a liquid chromatography column, a centrifuge, a packed bed adsorber, or a system configured to add additional concentrated reagents to the first dedicated container.

* * * * *